US008081769B2

(12) United States Patent
Fukuda et al.

(10) Patent No.: US 8,081,769 B2
(45) Date of Patent: Dec. 20, 2011

(54) APPARATUS FOR RECTIFYING RESONANCE IN THE OUTER-EAR CANALS AND METHOD OF RECTIFYING

(75) Inventors: Takashi Fukuda, Ome (JP); Toshifumi Yamamoto, Sagamihara (JP); Yutaka Oki, Ome (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 62 days.

(21) Appl. No.: 12/366,736

(22) Filed: Feb. 6, 2009

(65) Prior Publication Data

US 2009/0208027 A1 Aug. 20, 2009

(30) Foreign Application Priority Data

Feb. 15, 2008 (JP) ................................. 2008-035268

(51) Int. Cl.
*A61F 11/06* (2006.01)
*G10K 11/16* (2006.01)
*H03B 29/00* (2006.01)

(52) U.S. Cl. ........................................ 381/71.6; 381/74

(58) Field of Classification Search ................. 381/23.1, 381/317, 318, 320, 71.6, 71.14, 72, 74; 181/126, 181/130, 135; 600/559

See application file for complete search history.

(56) References Cited

U.S. PATENT DOCUMENTS 6,480,610 B1 11/2002 Fang et al.
6,658,122 B1 12/2003 Westermann et al.
7,668,325 B2 * 2/2010 Puria et al. .................... 381/322
2008/0123890 A1 * 5/2008 Peng ............................ 381/338
2008/0137878 A1 * 6/2008 Killion et al. ................ 381/71.6
2008/0159554 A1 * 7/2008 Sung et al. ................... 381/71.6

FOREIGN PATENT DOCUMENTS

| | | |
|---|---|---|
| JP | 53-42721 | 4/1978 |
| JP | 05-083797 | 4/1993 |
| JP | 09-185383 | 7/1997 |
| JP | 09-187093 | 7/1997 |
| JP | 10-294997 | 11/1998 |
| JP | 2000-050395 | 2/2000 |
| JP | 2000-092589 | 3/2000 |
| JP | 2001-285998 | 10/2001 |
| JP | 2002-209300 | 7/2002 |
| JP | 2008-177798 | 7/2008 |

OTHER PUBLICATIONS

Adachi, D. et al., "A Rating System of Headphones and Earphones Using Transfer Function of External Auditory Canal," *IEIC Technical Report* (*Institute of Electronics, Information and Communication Engineers*) 104(379):43-48 (2004).

Notice of Reasons for Rejection issued in Japanese Patent Application No. 2008-035268, mailed May 19, 2009 (6 pages).

* cited by examiner

*Primary Examiner* — Vivian Chin
*Assistant Examiner* — Con P Tran
(74) *Attorney, Agent, or Firm* — Finnegan, Henderson, Farabow, Garrett & Dunner, LLP

(57) ABSTRACT

According to one embodiment, an apparatus for cancelling resonance in an outer-ear canal, comprises an outer-ear canal model includes attenuator modules representing reflection coefficients of an earphone or headphone and an eardrum, and a delay module having a delay time corresponding to a distance between the earphone or headphone and the eardrum, an inverse-filter forming unit configured to form an inverse filter of the outer-ear canal model, and a convolution module configured to perform convolution on an impulse response from the inverse filter and a sound-source signal.

6 Claims, 9 Drawing Sheets

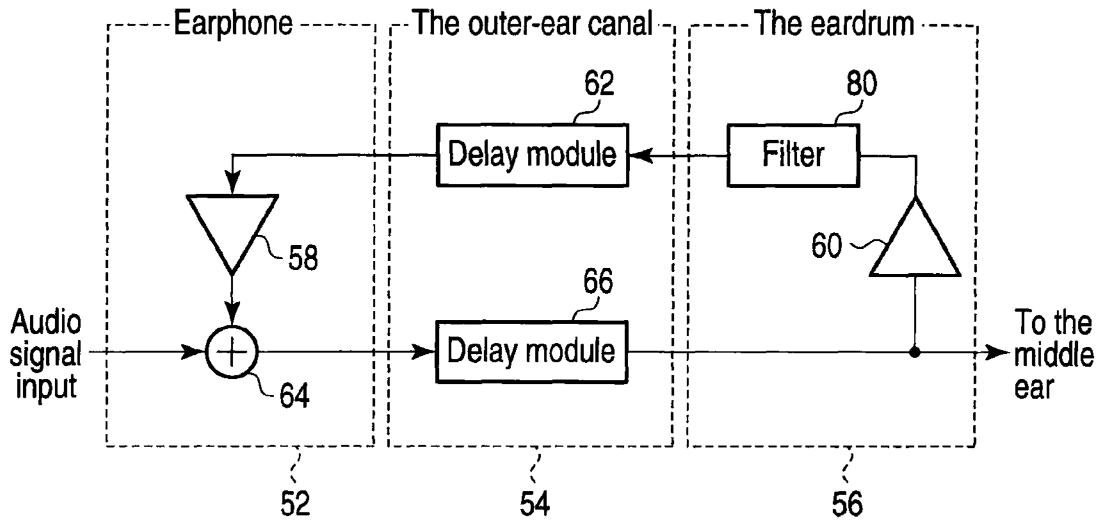
FIG. 12
FIG. 13A
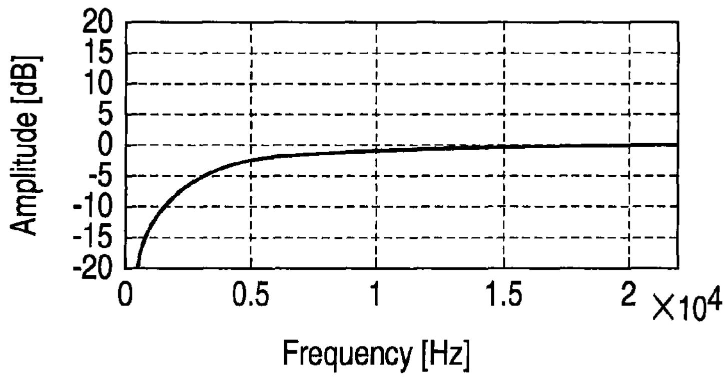
FIG. 13B
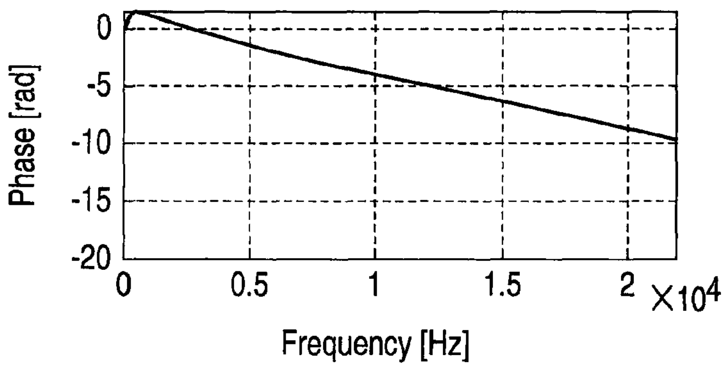

APPARATUS FOR RECTIFYING RESONANCE IN THE OUTER-EAR CANALS AND METHOD OF RECTIFYING

CROSS-REFERENCE TO RELATED APPLICATIONS

This application is based upon and claims the benefit of priority from Japanese Patent Application No. 2008-035268, filed Feb. 15, 2008, the entire contents of which are incorporated herein by reference.

BACKGROUND

1. Field

One embodiment of the present invention relates to an apparatus for cancelling resonance in the outer-ear canals and a method of cancelling resonance in the outer-ear canals.

2. Description of the Related Art

When a person is listening to music through an earphone or a headphone, resonance may develop between the eardrum and the earphone or the headphone. In this case, the music sounds strange to the listener. Various systems have been developed, which cancel such resonance. (See, for example, Jpn. Pat. Appln. KOKAI Publication No. 2000-92589, paragraph 0047 and FIGS. 1 and 2; Jpn. Pat. Appln. KOKAI Publication No. 2002-209300, paragraph 0040 and FIG. 1; and Jpn. Pat. Appln. KOKAI Publication No. 9-187093, paragraph 0024 and FIG. 2).

Jpn. Pat. Appln. KOKAI Publication No. 2000-(hereinafter referred to as Publication 1) discloses a technique of finding the position of an acoustic image outside a listener's head. FIGS. 2(*a*) and 2(*b*) of Publication 1 illustrate the principle of finding the position of the acoustic image outside the head. More precisely, FIG. 2(*a*) explains how sound coming from a speaker is picked up, and FIG. 2(*b*) explains how a twin earphone or a stereophonic headphone catches sound. In FIG. 2(*a*), reference numeral 101 denotes a sound-source signal, reference numeral 103 designates a speaker, and reference numeral 102 denotes two microphones set in the outer-ear canals, respectively. In FIG. 2(*b*), reference numeral 104 designates an earphone or a headphone, reference numeral 105 denotes a digital filter. Note that suffix L in $HRTF_L$ and suffix R in $HRTF_R$ stand for "left" and "right" respectively.

The principal of finding the position of the acoustic image outside the head lies in electrically formulate a transfer function identical to the transfer function for sound traveling to the listener's eardrum from a sound source that exists outside the listener's head.

However, it is difficult for an electric signal emanating from a living body to pick up the vibration the eardrum are undergoing as sound waves. Hence, the transfer function of the electric signal traveling to the eardrum can hardly be measured accurately from the sound-source signal 101 shown in FIG. 2(*a*). This is why the listener sets small microphones 102 in his or her outer-ear canals, respectively, and the transfer function of the electric signal, i.e., head related transfer functions (HRTFs) in the left and right ears, is measured from the sound-source signal 101 that has been input to the speaker 103 by using these microphones 102.

The speaker 103 has a specific frequency characteristic. The true transfer function of the electric signal traveling from the input of the speaker 103 to the microphones 102 is therefore given as HRTF/SPTF, where SPTF is the transfer function for the speaker 103.

In the system of FIG. 2(*b*) of Publication 1, the twin earphone or stereophonic headphone 104 may be used to provide a transfer function that is equivalent to function HRTF/SPTF. To provide this transfer function, the transfer function of a signal traveling from the earphone or headphone 104 to the microphones 102 set in the outer-ear canals, i.e., ear-canal transfer function (ECTF), is measured. If the product of this transfer function ECTF and the transfer function of the digital filter 105 is equal to the transfer function HRTF/SPTF, aural signal identical to the speaker signals can be reproduced at the microphones 102 set in the outer-ear canals.

In the system disclosed in Publication 1, an ex-head sound-image locating means of the type shown in FIG. 5 is used to measure the outer-ear canal transfer function, i.e., transfer function attained while the listener is wearing the earphone or headphone 104. The outer-ear canal transfer function thus measured is corrected by using an adaptive equalization filter.

Microphones 3 that pick up the sound in the outer-ear canals are formed integral with the speakers of the earphone or headphone, as is illustrated in FIG. 1 of Publication 1. A digital filter 11 is used, which stores an impulse response having transfer function HRTF/SPTF that has been measured by such a configuration as shown in FIG. 2(*a*) of Publication 1.

A band-pass filter 13 is provided, for the following reason. An adaptive filter 12 and the transfer function ECTF are connected in series, and the output of this series circuit may be an impulse. In this case, the transfer function of the adaptive filter 12 is inverse to the function ECTF, i.e., 1/ECTF. However, the function ECTF pertains to both a speaker 1 and the microphones 3 and therefore attenuates outside a specific band. Hence, the transfer function of the adaptive digital filter 12, which is inverse to the transfer function ECTF, attains a large gain outside the specific band.

The tap coefficient or impulse response of the adaptive digital filter 12 can therefore be stably acquired if the result of the convolution performed on the impulse responses of the filter 12 and ECTF is regarded as the impulse response of the band-pass filter 13. In other words, if the band of the band-pass filter 13 is narrower than that of the adaptive digital filter 12, a subtracter 14 will cancel the ex-band part of the transfer function of the adaptive digital filter 12. As a result, a stable solution can be obtained.

In the system disclosed in Publication 1, an adaptive equalization filter is used to correct the outer-ear canal transfer function. In order to correct this transfer function accurately, the microphones 3 must exhibit flat frequency characteristic within the band. This is because the music will sound strange at the eardrum if the adaptive digital filter 12 generates an inverse transfer function from the transfer function ECTF that pertains to the characteristic of the microphones 3. Further, the position of the microphones 3 is important and should therefore be carefully determined. If the microphones 3 are located at the eardrums, no problems will arise. If the microphones 3 are located at the distal ends of the twin earphone or headphone (not at the ends of the outer-ear canals), however, it will pick up sound not at the nodes of a standing sound wave. Consequently, the microphones 3 will acquire such a characteristic that they catch sound at the dips of the standing sound wave. The music will inevitably sound strange to the listener.

Jpn. Pat. Appln. KOKAI Publication No. 2002-209300 (hereinafter referred to as Publication 2) discloses a technique of cancelling the influence of standing waves formed in a twin earphone or headphone and at the listener's eardrum. To cancel the standing waves, the vibration signal emanating from either eardrum should be measured to determine the sound-transfer characteristic in the outer-ear canals. It is difficult, however, to set microphones at the eardrums to detect the vibration signals in the vicinity of the eardrums. In the technique disclosed in Publication 2, the microphones are set at the eardrums of a pseudo-head, in order to measure the outer-ear ear canal transfer function. Based on the characteristic measured, a filter is designed, which can cancel the standing wave that extends from either eardrum and the earphone or headphone.

However, the length and acoustic impedance of outer-ear canals differ, from person to person. The transfer function in the outer ears therefore differs, on the individual basis. It follows that the position where resonance frequency is attained differs, on individual basis, too. Further, the resonance frequency is attained at a position in the left ear, and at a different position in the right ear. The outer-ear canal transfer function should therefore be corrected in accordance with the physical characteristics of the ears of each person. Hence, the characteristic determined by using the pseudo-head can hardly serve to manufacture a filter that proves satisfactory to all users. In view of this, filters of different characteristics may be prepared so that the user may select one that he or she finds best. Here arises a problem. The user can hardly select a filter he or she thinks the best for him or her. Moreover, the filter the user selects can scarcely work flawlessly.

Jpn. Pat. Appln. KOKAI Publication No. 9-187093 (hereinafter referred to as Publication 3) discloses a system that has an electro-acoustic converting means and a resonance-frequency component reducing means connected to the input of the electro-acoustic converting means. The resonance-frequency component reducing means is configured to reduce a resonance-frequency component of a frequency near the resonance frequency in human ears. Thus, the means prevents a decline in the hearing ability of the user who habitually listens to laud music through an earphone or a headphone. That is, the resonance-frequency component reducing means prevents the sound level of the resonance frequency in the ears from increasing excessively. The resonance-frequency component reducing means is an electrical circuit that has a resister, to which a parameter for reducing the resonance-frequency component detected is set. However, no parameters are specified in Publication 3. Methods of determining such a parameter are known in the art. One method is to use a filter inverse to the resonance data actually acquired as described in Publication 1. Another method is to provide a filter similar to the data acquired by, for example, a parametric equalizer. These methods are, however, disadvantageous in the following respects.

1) Since microphones cannot be located at the eardrums, the characteristics of the ears cannot be accurately measured. If the inverse filter designed on the basis of the characteristics measured is subjected to convolution, the resulting sound will be degraded in quality.

2) Many parameters are applied, rendering the tuning extremely difficult. Desirable characteristics may not be attained in some cases. Even if desirable characteristics are attained, it will be very difficult to determine the phase accurately.

As has been described, the conventional apparatus for rectifying resonance in the outer-ear canals cannot easily rectify the resonance in accordance with the structure of the outer-ear canals of each person.

BRIEF DESCRIPTION OF THE SEVERAL VIEWS OF THE DRAWINGS

A general architecture that implements the various feature of the invention will now be described with reference to the drawings. The drawings and the associated descriptions are provided to illustrate embodiments of the invention and not to limit the scope of the invention.

FIG. 12 is an exemplary diagram showing another model of sound-wave propagation in an outer-ear canal;

FIGS. 13A and 13B are exemplary graphs showing the frequency characteristic of a high-pass filter, which represents the frequency-dependency of the acoustic impedance of the eardrum used in the model of FIG. 12;

DETAILED DESCRIPTION

Various embodiments according to the invention will be described hereinafter with reference to the accompanying drawings. In general, according to one embodiment of the invention, an apparatus for cancelling resonance in an outer-ear canal, comprises an outer-ear canal model comprising attenuator modules representing reflection coefficients of an earphone or headphone and an eardrum, and a delay module having a delay time corresponding to a distance between the earphone or headphone and the eardrum; an inverse-filter forming unit configured to form an inverse filter of the outer-ear canal model; and a convolution module configured to perform convolution on an impulse response from the inverse filter and a sound-source signal.

Figure 1A:
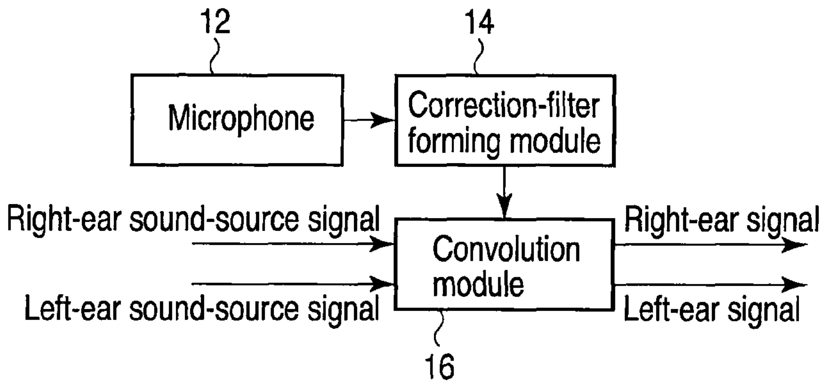
FIGS. 1A and 1B are exemplary diagrams outlining how the resonance in the outer-ear canals is cancelled according to an embodiment of the present invention.
Figure 1B:
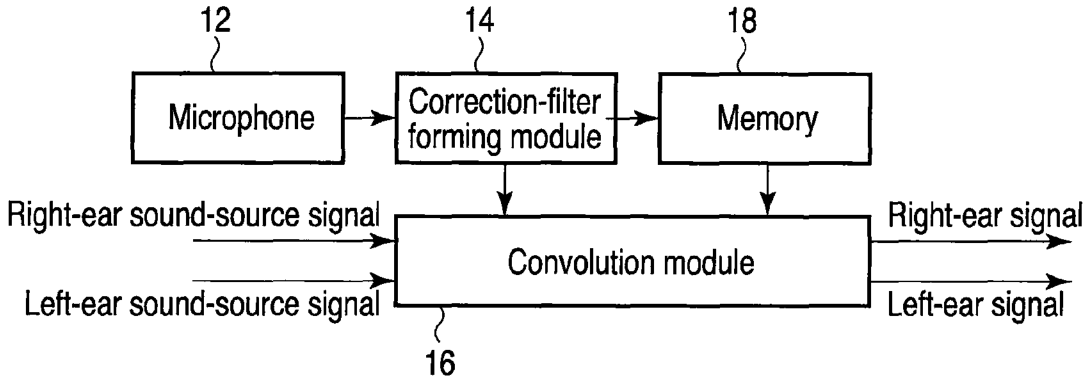

According to an embodiment, FIGS. 1A and 1B show two alternative configurations that an apparatus according to this invention may have. In either configuration, a microphone 12 picks up an audio signal, which is input to a correction-filter forming module 14. Meanwhile, a right-ear sound-source signal and a left-ear sound-source signal are input to a convolution module 16. The correction-filter forming module 14 analyzes the audio signal input to it, forming a correction filter. The correction filter has such a frequency characteristic as will form dips at a frequency near the resonance frequency in order to cancel the resonance. The tap coefficient of the correction filter is set in the convolution module 16 in the configuration of FIG. 1A. In the configuration of FIG. 1B, the tap coefficient is first written in a memory 18 and then set in the convolution module 16. Nonetheless, in the configuration of FIG. 1B, too, the tap coefficient may be subjected to convolution, not written in the memory 18 at all. The convolution module 16 uses the tap coefficient thus set, performing convolution on the right-ear and left-ear sound-source signals. As a result, signal not influenced by the resonance are thereby attained.

Figure 2:
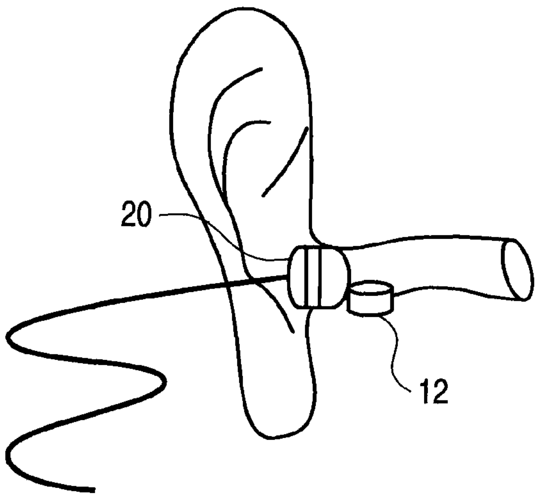
FIG. 2 is an exemplary diagram showing a position the microphone in the system of FIG. 1A or the system of FIG. 1B.
Figure 3:
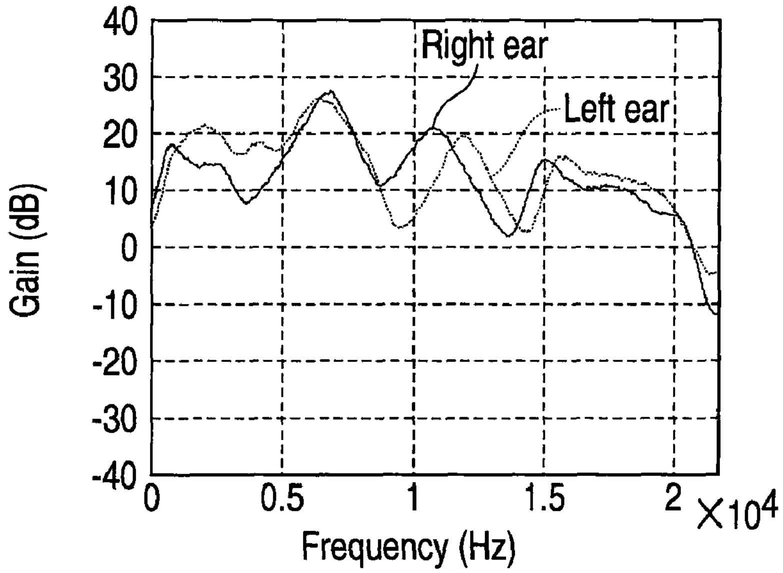
FIG. 3 is an exemplary graph representing the frequency characteristics in the left and right ears of a person, which have been determined from the sound picked up by the microphone show in FIG. 1A or FIG. 1B.
Figure 4:
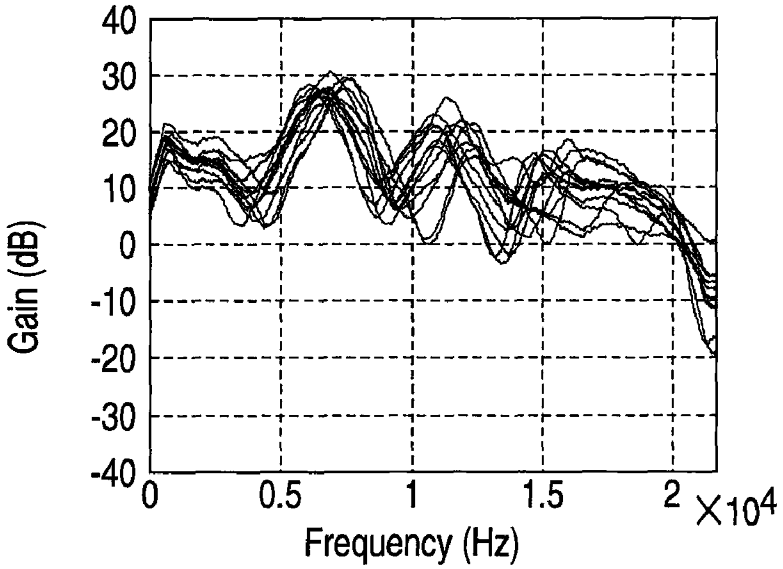
FIG. 4 is an exemplary graph representing the frequency characteristics in the left ears of several persons.

As shown in FIG. 2, the microphone 12 is fixed to an earphone or headphone 20. Since the microphone 12 is arranged not at the end of the outer-ear canal to detect the characteristic of the ear, it picks up sound at the nodes of a standing wave. The characteristic that the microphone 12 detects therefore has such dips as shown in FIGS. 3 and 4. The characteristic detected is inevitably different from the characteristic that may be detected at the eardrum. FIG. 3 shows the frequency characteristics in the left and right ears of a person. FIG. 4 shows the frequency characteristics in the left ears of several persons.

Figure 5:
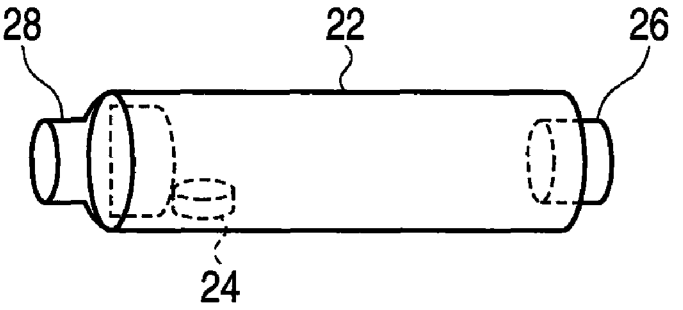
FIG. 5 is an exemplary diagram explaining an experiment conducted by using a pseudo-outer ear, in order to compare the frequency characteristic of an eardrum microphone with that of an inner microphone.
Figure 6:
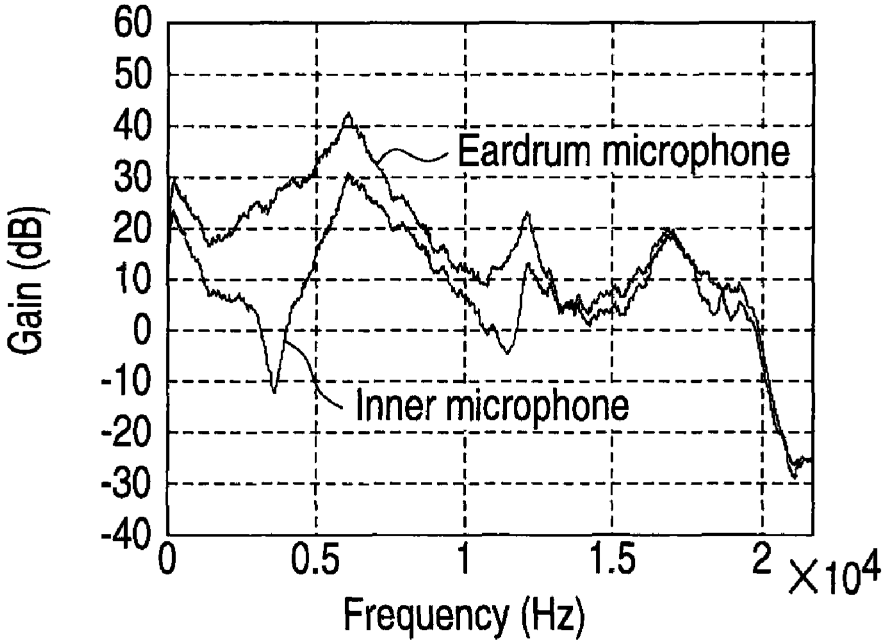
FIG. 6 is an exemplary graph representing the frequency characteristics of the eardrum microphone and inner microphone, which have been determined in the experiment.

If the microphone 12 is arranged not at the end of the outer-ear canal, the characteristic it detects will differ from those shown in FIGS. 3 and 4. Nonetheless, the peak frequency (i.e., resonance frequency) detected by the earphone or headphone 20 is almost the same as the peak frequency detected at the eardrum. With reference to FIG. 5 and FIG. 6, it will be described why the frequency characteristic detected near the eardrum is equal to the resonance frequency detected at a position other than the eardrum. FIG. 5 is a diagram explaining an experiment conducted by using a pseudo-outer ear 22. The pseudo-outer ear 22 is a hollow cylinder shaped like a human outer-ear canal. In the experiment, a miniature inner microphone 24 was inserted in the pseudo-outer ear 22, an eardrum microphone 26 was attached to one end of the cylinder, and an earphone or headphone 28 was attached to the other end of the cylinder. The earphone or headphone 28 output a uniform white noise. The inner microphone 24 and the eardrum microphone 26 picked up the white noise. The noises the inner microphone 24 and the eardrum microphone 26 picked up were compared in terms of spectrum. FIG. 6 is a graph that represents the frequency characteristics of the eardrum microphone 26 and inner microphone 24. As seen from FIG. 6, the characteristic of the inner microphone 24 has indeed dips at the nodes of the standing wave, but is almost the same as the characteristic detected by the eardrum microphone 26 and inner microphone 24. Since the frequency characteristic detected by the microphone 12 changes in accordance with the position where the microphone 12 is arranged, any inverse filter having the frequency characteristic detected by the microphone 12, if provided, cannot work accurately. Hence, the resonance can hardly be canceled as desired. The resonance frequency detected is correct, nevertheless. The resonance can therefore be canceled if only the resonance frequency detected is utilized.

The microphone 24 may be arranged in the earphone or headphone 28 or located remote from the earphone or headphone 28. In either case, the microphone 24 must be so positioned that no dips may exist at the peak frequency (i.e., resonance frequency).

Figure 7:
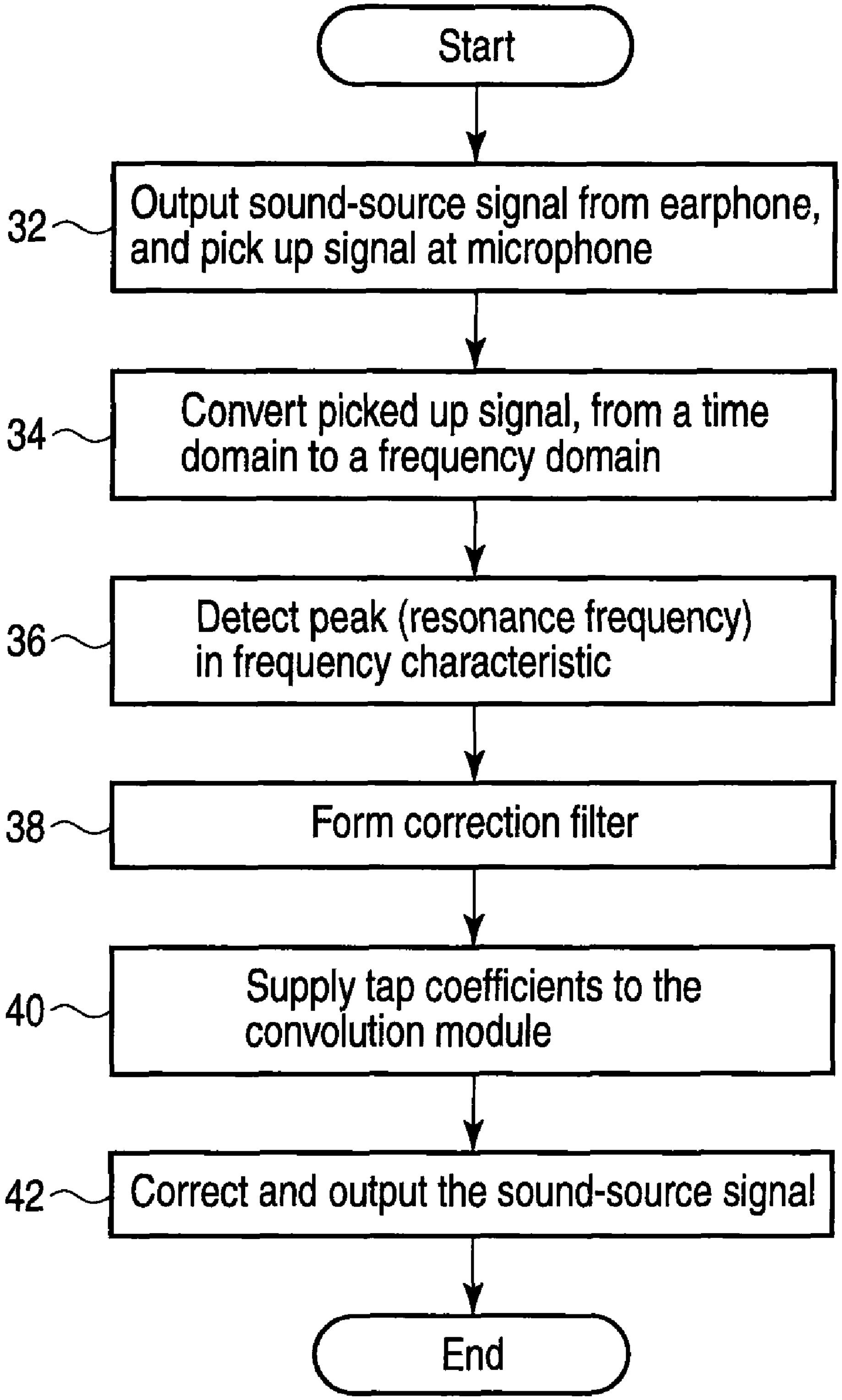
FIG. 7 is an exemplary flowchart explaining the operation of the correction-filter forming module shown in FIG. 1.

FIG. 7 is a flowchart explaining the operation of the correction-filter forming module 14. First, as shown in FIG. 2, the earphone or headphone 20 to which the microphone 12 attached is inserted into the outer-ear canal and outputs a sound-source signal, which the microphone 12 picks up (Block 32). The sound-source signal that the earphone or headphone 20 outputs is preferably white noise that has a uniform frequency spectrum. Nonetheless, the sound-source signal may alternatively be pink noise that attenuates in a specific band. Still alternatively, the sound-source signal may be a time-stretched pulse (TSP).

In Block 34, the audio signal is converted from a time domain to a frequency domain. In Block 36, resonance peaks are detected on the frequency axis. In view of the frequency characteristic shown in FIG. 3, two resonance peaks are detected for the left ear and for the right ear. For example, the first peak falls within the range of 5 kHz to 10 kHz, and the second falls within the range of 10 kHz to 15 kHz.

Two correction filters are formed for the left and right ears, respectively, so that dips may be formed at peak frequencies in order to cancel the resonance peaks for the left and right ears (Block 38). The correction filters may be formed by a parametric equalizer or a graphic equalizer. In this embodiment, a model is used to form the correction filters, as will be explained later in detail.

In Block 40, the correction-filter forming module 14 generates tap coefficients of correction filters for the left and right ears, respectively, and then supplies the tap coefficients, either directly or via the memory 18, to the convolution module 16.

The convolution module 16 performs convolution on the data items transferred from the correction-filter forming module 14 or memory 18 and the left- and right sound-source signals. (Note that the data items are the two tap coefficients representing impulse responses of the left and right ears, respectively). The convolution module 16 therefore generates a left-ear signal and a right-ear signal, each no long having a resonance component.

Thus, two filters are formed, which cancel the resonance peaks detected in the outer-ear canals of the listener. Then, the tap coefficients representing the impulse responses of the left and right ears are set in the convolution module 16. The left and right sound-source signals are then subjected to convolution. As a result, the frequency peaks shown in FIG. 3 are rendered flat.

So far described is a case where two microphones are arranged in the left and right modules of an earphone or headphone and detect the characteristics of the left and right ears, and two correction filters are formed for the left and right ears, respectively. Nonetheless, the characteristic of only one ear may be detected, and the correction filter formed based on this characteristic may be applied to both the left sound-source signal and the right sound-source signal.

The process of forming such correction filters may be performed every time an audio player, for example, is activated, or every time the user instructs. Alternatively, this process may be performed when the audio player is activated after a time the user set by the user has elapsed.

As described above, the microphone 12 for detecting the characteristics of the outer-ear canals, the correction-filter forming module 14, and the convolution module 16 for performing convolution on the sound-source signals constitute an integrated module. Nonetheless, these components 12, 14 and 16 need not be integrated. For example, the sound-source signals the microphone 12 picks up may be taken into an apparatus such as a personal computer (PC). If this is the case, the personal computer execute software, forming correction filters.

To play back the music, the convolution module 16 may be incorporated in the audio player and corrects the left-ear and right-ear signals in real time, thus playing back the music. Alternatively, the PC may execute software, thereby to correct the sound-source signals, and the signals thus corrected may then be transferred to the audio player.

In the apparatus for canceling the resonance in the outer-ear canals, shown in FIG. 1A or 1B, correction filters are formed, which have dips at the peak frequencies of the sound picked up. The apparatus need not have adaptive equalization filters in order to correct the transfer functions measured of the outer-ear canals. Thus, the apparatus can cancel the resonance at the earphone or headphone and the eardrum, without using expensive microphones at the eardrum. Since correction filters can be formed even if the microphones are not arranged at appropriate positions, the time required to design the apparatus can be shortened. Further, the microphones fixed to the earphone or headphone detect the characteristic of the resonance developing between the earphone or headphone and the eardrum of the wearer of the earphone or headphone, and correction filters adapted to the characteristic detected are formed. The filters thus formed can cancel the resonance in the outer-ear canals, which differs in accordance with the physical characteristics of the user's outer-ear canals and with the state in which the user wears the earphone or headphone. That is, the two correction filters can cancel the resonance in the outer-ear canals, because they have been formed on the basis of the characteristic of the left ear and that of the right ear, respectively.

How the correction-filter forming module 14 shown in FIGS. 1A and 1B form correction filters (in Block 38 shown in FIG. 7) will be explained. As pointed out above, the frequency characteristic changes, depending on the position where the microphone 12 is arranged. By contrast, the resonance frequency does not change at all. Therefore, correction filters are formed on the basis of the resonance frequency only, which has been detected from the frequency characteristic detected. Thus, the data acquired (i.e., frequency characteristic) is not used to form correction filters in the present embodiment. Instead, a model of sound-wave propagation in an outer-ear canal is formulated by using parameters such as the reflection coefficient pertaining to the earphone or headphone and the eardrum and the time a sound wave requires traveling between the earphone or headphone and either eardrum. Filters inverse to this sound-wave propagation model are formed and used, thereby canceling the resonance in the user's outer-ear canal.

Figure 8:
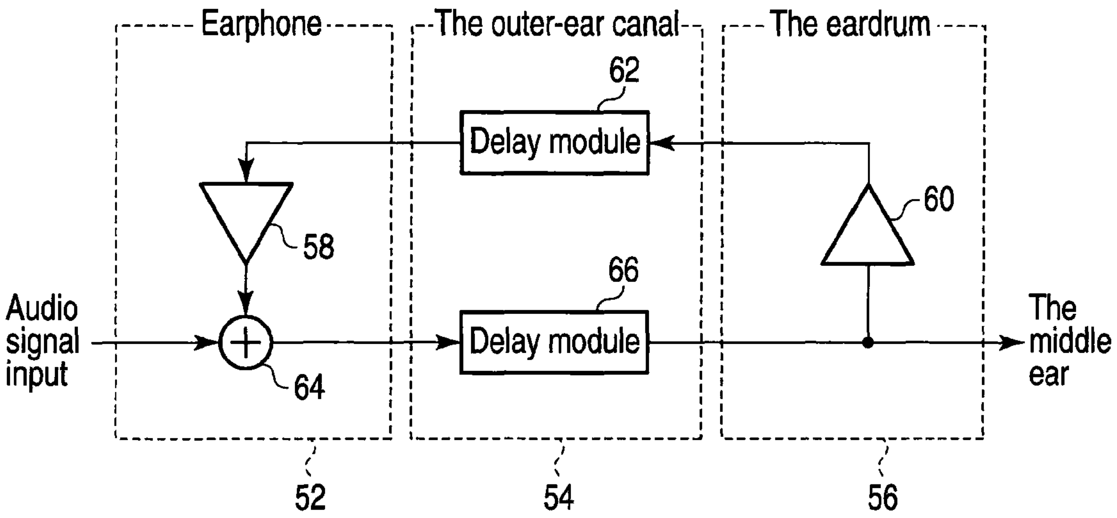
FIG. 8 is an exemplary diagram showing a model of sound-wave propagation in an outer-ear canal.

FIG. 8 shows a model of sound-wave propagation in an outer-ear canal. As shown in FIG. 8, the sound-wave propagation model comprises attenuator modules 58 and 60, delay modules 62 and 66, and an adder module 64. The attenuator module 60 represents the reflection coefficient of the eardrum. The attenuator module 58 represents the reflection coefficient of an earphone or headphone. The delay modules 62 and 66 have a delay time corresponding to the distance between the earphone or headphone and the eardrum. The distance is proportional to the time a sound wave requires to travel between the earphone or headphone and the eardrum. The adder module 64 adds the input audio signal coming from the earphone or headphone and the signal reflected by the earphone or headphone (i.e., the output of the attenuator module 58). The reflection coefficient of the earphone or headphone and the reflection coefficient of the eardrum change from person to person. This model utilizes reflection coefficients of ordinary values. The distance between the earphone or headphone and the eardrum can be determined by first finding the wavelength of the sound wave from the resonance frequency detected and then by calculating the distance from the sound velocity and the wavelength thus found.

Figure 9A:
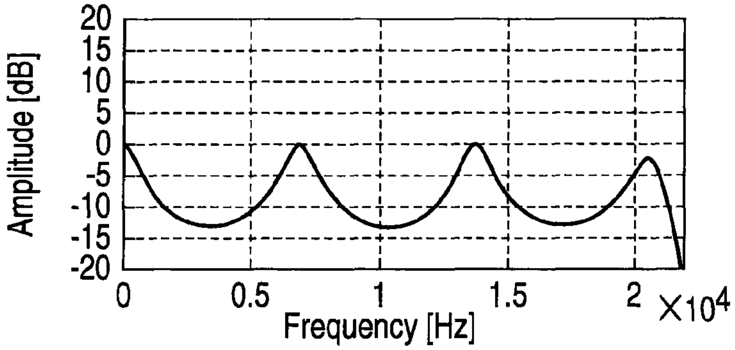
FIGS. 9A and 9B are exemplary diagrams showing the acoustic frequency characteristics determined of the model of FIG. 8.
Figure 9B:
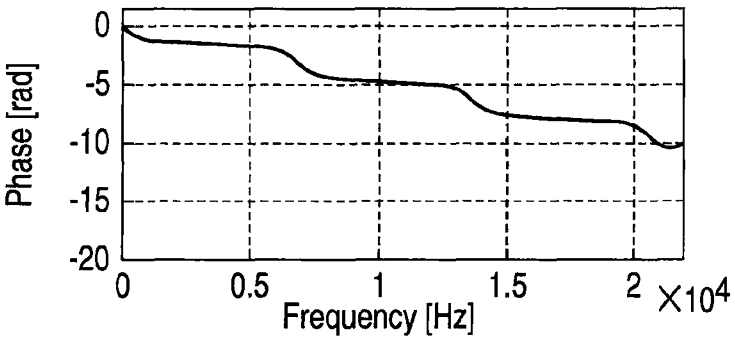

The sound-wave propagation model thus configured provides such acoustic characteristics of the outer-ear canal as illustrated in FIGS. 9A and 9B. FIG. 9A shows the amplitude-frequency characteristic. FIG. 9B shows the phase-frequency characteristic.

Figure 10:
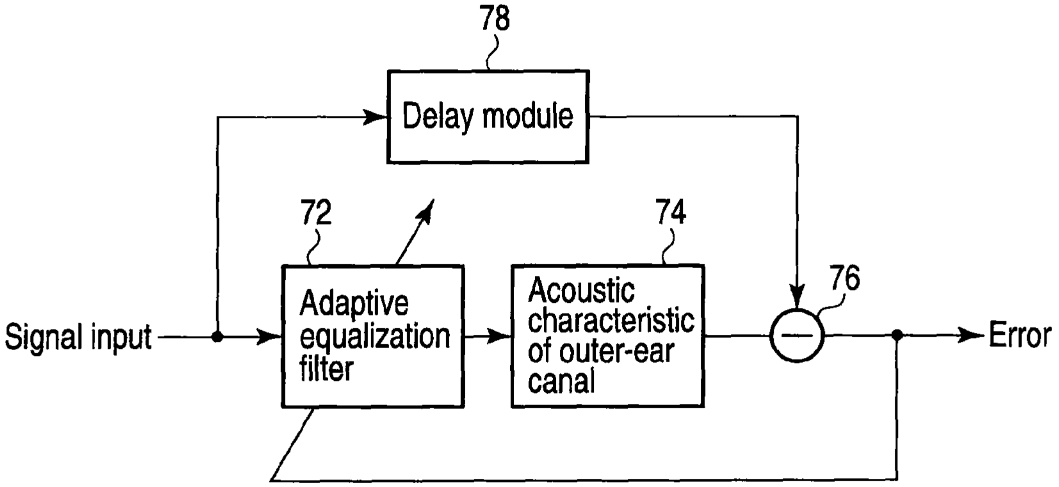
FIG. 10 is an exemplary diagram outlining a method of forming an inverse filter by using the model of FIG. 8.

Next, an inverse filter is formed based on a model shown in FIG. 10 using the acoustic characteristics of the outer-ear canal, thus acquired. As shown in FIG. 10, a signal is input to an adaptive equalization filter module 72 and a delay module 78. The output of the adaptive equalization filter module 72 is input to a filter module 74 that represents the acoustic characteristics of the outer-ear canal (i.e., model of FIG. 8). The delay time of the delay module 78 is the time that the input signal requires to pass first through the adaptive equalization filter module 72 and then through the outer-ear-canal acoustic characteristic filter 74. Hence, the input signal coming through the delay module 78 has an expected value of the input signal coming through the adaptive equalization filter module 72 and the outer-ear-canal acoustic characteristic filter module 74. The outputs of the delay module 78 and outer-ear-canal acoustic characteristic filter module 74 are input to a subtracter module 76. The output of the subtracter module 76 is supplied to the adaptive equalization filter 72, which achieves self learning in order to minimize the output error of the subtracter module 76. The characteristic that the adaptive equalization filter module 72 acquires when the output error of the subtracter module 76 becomes minimal is a filter inverse to the outer-ear-canal acoustic characteristic filter module 74. The adaptive equalization filter 72 may be selected from various types. In the present embodiment, the adaptive equalization filter module 72 is a filter module that receives white noise as input signal and uses the least-mean-square (LMS) as adaptation algorithm.

Figure 11A:
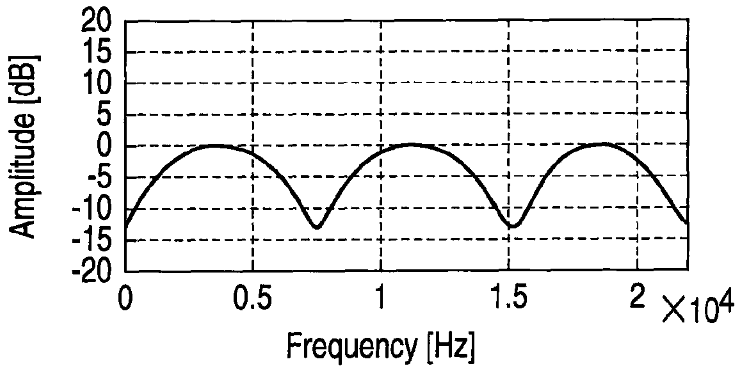
FIGS. 11A and 11B are exemplary graphs representing the frequency characteristic of the inverse filter shown in FIG. 10.
Figure 11B:
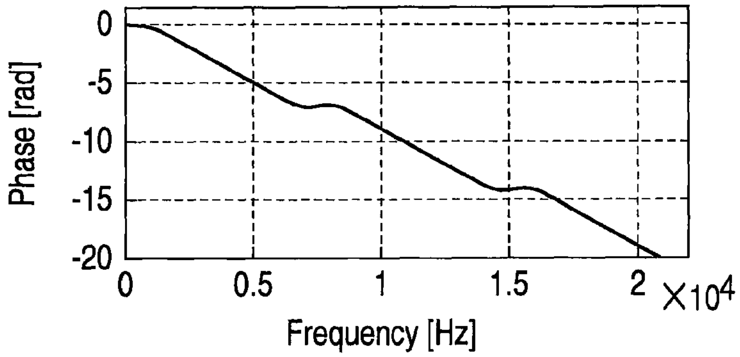

Assume that the filter module 74 has the outer-ear-canal acoustic characteristic shown in FIGS. 9A and 9B. Then, the adaptive equalization filter module 72 has such a characteristic as shown in FIGS. 11A and 11B. If the correction-filter forming module 14 forms a correction filter having the characteristic shown in FIGS. 11A and 11B, the convolution module 16 can accurately cancel the resonance specific to the outer-ear canal acoustic characteristic of the user.

The process described above is performed for both the left ear and the right ear. Two correction filters can thereby be formed for the left and right ears, respectively.

A method of improving accuracy of measuring the characteristic will be described. In the model of FIG. 8, resonance (peak) occurs at a low frequency near 0 Hz as seen from the frequency characteristic shown in FIG. 9A, though resonance usually does not occur at such a low frequency. As a result, the inverse filer formed from the model inevitably attenuates the low-band component as shown in FIG. 11A, ultimately degrading the sound quality. This is probably because the frequency dependency of acoustic impedance is not taken into consideration. A reflection coefficient of the eardrum changes depending on frequency in the model of FIG. 8. Therefore, in order to impart the frequency dependency of acoustic impedance, a model of sound-wave propagation in an outer-ear canal (see FIG. 12) is utilized, which differs from the model of FIG. 8 in that a filter module 80 is connected to the output of the attenuator module 60 that represents the reflection coefficient of the eardrum.

As is known in the art, the polymer constituting the eardrum exhibits elasticity that is low mainly at low frequencies and increases as the frequency rises. This is why the model of FIG. 12 has a high-pass filter module 80 that has the amplitude characteristic and phase characteristic shown in FIG. 13A and FIG. 13B, respectively.

Figure 14A:
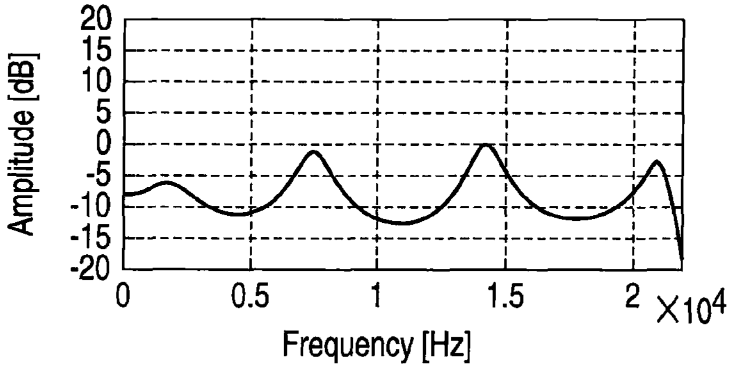
FIGS. 14A and 14B are exemplary graphs representing the acoustic frequency characteristics determined of the model of FIG. 12.
Figure 14B:
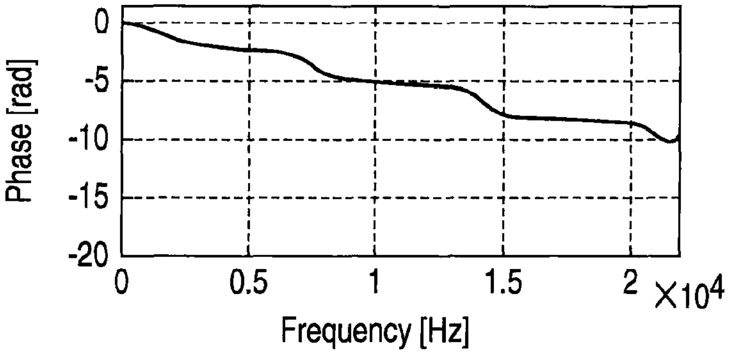
Figure 15A:
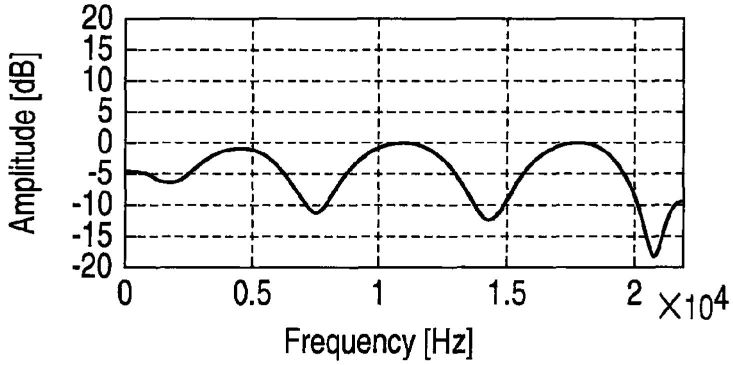
FIGS. 15A and 15B are exemplary graphs representing the frequency characteristic of the inverse filter provided on the basis of the model shown in FIG. 12.
Figure 15B:
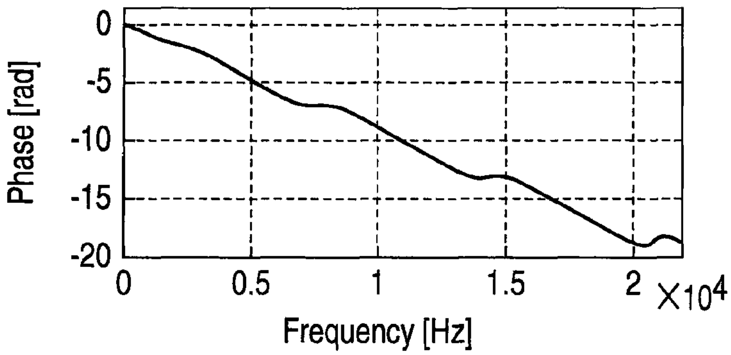

As a result, the resonance at a low band is suppressed as seen from the amplitude and phase characteristics of the outer-ear canal, obtained from the model of FIG. 12 and illustrated in FIG. 14A and FIG. 14B. Thus, an inverse filter can be provided, which has amplitude and phase characteristics having no dips in the low band as shown in FIG. 15A and FIG. 15B. The inverse filer can reduce the quality degradation of the sound, which may occur in the model shown in FIG. 8.

The use of the model of FIG. 8 or the model of FIG. 12 can provide desirable characteristics, merely by turning the reflection coefficient and the length. In addition, an inverse filter having an appropriate phase characteristic can be formed based on a sound-wave propagation model which exhibits the physical characteristics of the user's outer-ear canals. Even if the physical characteristics of the outer-ear canals cannot be accurately acquired, it is possible to form inverse filter that little degrade the sound quality. Using the resonance data detected of the user, the physical properties specific to the user's outer-ear canals and eardrum can be well reflected in the correction filters. Further, the difference between the left and right ears in terms of acoustic characteristic can be reflected in the correction filters, on the basis of the resonance data detected of the user's left and right ears. Moreover, the difference in resonance characteristic between the various types of earphones or headphones and between the states in which the user wears the earphone or headphone can be reflected in the correction filters.

Figure 16:
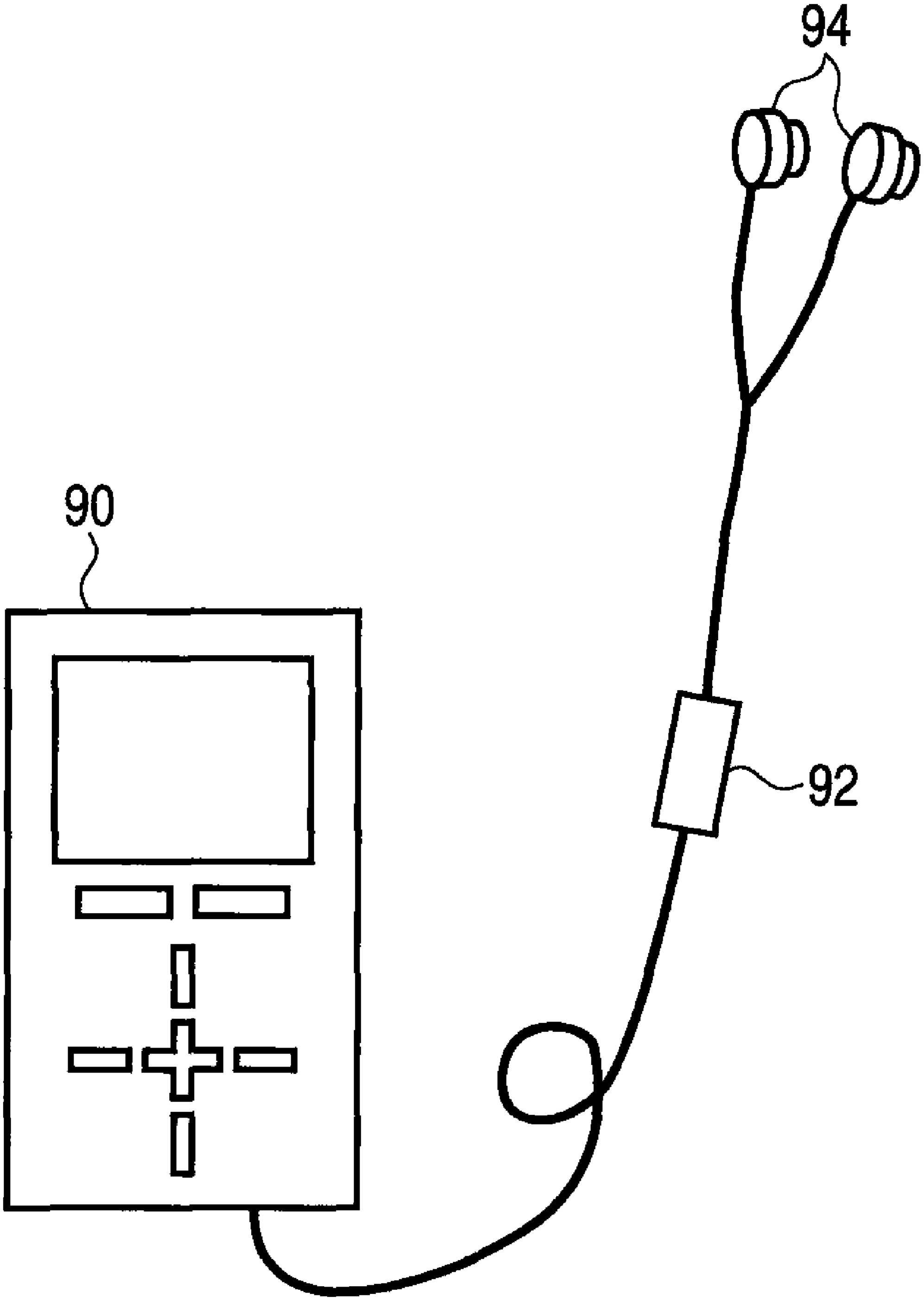
FIG. 16 is an exemplary diagram showing an apparatus incorporating the system of FIG. 1A or 1B.

The positions where the correction-filter forming module 14 and convolution module 16, both shown in FIGS. 1A and 1B, are formed will be explained with reference to FIG. 16.

The correction-filter forming module 14 and convolution module 16 may be incorporated in an audio player 90. In this case, the tap coefficient generated in the correction-filter forming module 14 is stored in the memory 18, and the sound-source signal read from a flash memory (not shown) or a hard disk (not shown) is corrected in the convolution module 16 and is then output to an earphone or headphone 94. Alternatively, the sound-source signal may be corrected before it is downloaded and may then be stored in a memory (not shown). The correction-filter forming module 14 and convolution module 16 may be incorporated in a remote controller 92 or the earphone or headphone 94. In either case, the microphone 12 is fixed to the earphone or headphone 20 as is illustrated in FIG. 2.

As has been explained thus far, this embodiment detects the resonance frequency from the frequency characteristics of the user's outer-ear canals, acquired by the microphones arranged at given positions in the outer-ear canals. A sound-wave propagation model comprises attenuator modules representing the reflection coefficient of the earphone or headphone and the reflection coefficient of the eardrum, and delay modules having a delay time corresponding to the distance between the earphone or headphone and the eardrum. The time corresponding to the distance between an eardrum and an earphone or headphone, which has been obtained from the resonance frequency detected, is set in the delay times of the delay modules. Using this model, an inverse filter module is adaptively equalized (identified). The inverse filter module corrects the frequency characteristic of a sound-source signal, thereby accurately cancelling the resonance specific to the acoustic characteristics of outer-ear canals of any user.

If inverse filter module formed not on the basis of the data acquired without using such a model is employed to cancel the resonance, the resonance frequency cannot be accurately measured because the microphones cannot be arranged at the eardrum. When resonance is cancelled, using this model, the sound quality will be degraded.

Moreover, a high-pass filter module may be added to the above-mentioned model in order to impart the frequency dependency of acoustic impedance. In this case, an inverse filter module can be provided, which has amplitude and phase characteristics having no dips in the low band. This inverse filer module can reduce the quality degradation of the sound.

Generally, a parametric equalizer may be used to form an inverse filter module. In this case, however, the inverse filter module may fail to have desirable characteristic, because the tuning is difficult to accomplish due to the many parameters involved. Even if the inverse filter module exhibits desirable characteristics, it can hardly reflect the phase accurately. Consequently, the phase data inevitably assumes an unnatural state (undergoing an extraordinary phase rotation) when the resonance is cancelled. Nevertheless, the model according to the present embodiment can acquire accurate phase data, as well.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The various modules of the systems described herein can be implemented as software applications, hardware and/or software modules, or components on one or more computers, such as servers. While the various modules are illustrated separately, they may share some or all of the same underlying logic or code. The accompanying claims and their equivalents are intended to cover such forms or modifications as would fall within the scope and spirit of the inventions.

What is claimed is:

1. An apparatus for cancelling resonance in an outer-ear canal, comprising:

a model of the outer-ear canal, the model comprising attenuator modules representing reflection coefficients of an earphone or headphone and an eardrum, and a delay module having a delay time corresponding to a distance between the earphone or headphone and the eardrum;

an inverse-filter forming module configured to form an inverse filter of the model of the outer-ear canal; and an arithmetic module configured to perform convolution on an impulse response from the inverse filter and a sound-source signal, wherein the delay time of the delay module is determined from a resonance frequency acquired by detecting a peak of a frequency characteristic measured in the outer-ear canal having the earphone or headphone by collecting by a microphone attached to the earphone or headphone a sound-source signal generated from the earphone or headphone.

2. The apparatus of claim 1, wherein the model of the outer-ear canal comprises a filter having a frequency characteristic of an acoustic impedance of the eardrum.

3. The apparatus of claim 2, wherein the filter comprises a high-pass filter.

4. The apparatus of claim 1, wherein the model of the out-ear canal comprises:

a first attenuator representing the reflection coefficient of the earphone or headphone;

a second attenuator representing the reflection coefficient of the eardrum;

a first delay configured to delay an output of the second attenuator by a time a sound wave requires to travel between the earphone or headphone and the eardrum and to input an output to the first attenuator;

an adder configured to add an output of the first attenuator and an input audio signal; and a second delay configured to delay an output of the adder by the time a sound wave requires to travel between the earphone or headphone and the eardrum, and wherein the output of the second attenuator is input to the second attenuator.

5. The apparatus of claim 1, wherein the frequency characteristic is measured for a user of the apparatus and for left and right ears of the user.

6. The apparatus of claim 1, wherein the inverse-filter forming module is configured to input an input signal to a serial circuit formed of an adaptive equalization filter and the model of the outer-ear canal, thereby adjusting the adaptive equalization filter to minimize a difference between an ideal input signal and the output of the serial circuit.

* * * * *